United States Patent
Ramsey et al.

[11] Patent Number: 5,858,187
[45] Date of Patent: Jan. 12, 1999

[54] APPARATUS AND METHOD FOR PERFORMING ELECTRODYNAMIC FOCUSING ON A MICROCHIP

[75] Inventors: John Michael Ramsey; Stephen C. Jacobson, both of Knoxville, Tenn.

[73] Assignee: Lockheed Martin Energy Systems, Inc., Oak Ridge, Tenn.

[21] Appl. No.: 721,264

[22] Filed: Sep. 26, 1996

[51] Int. Cl.[6] .......................... G01N 27/26; G01N 27/447
[52] U.S. Cl. .......................... 204/452; 204/451; 204/601; 204/604
[58] Field of Search ................................... 204/451, 452, 204/453, 454, 455, 601, 602, 603, 604, 605

[56] References Cited

U.S. PATENT DOCUMENTS 5,439,578  8/1995  Dovichi et al. .................. 204/603
5,529,679  6/1996  Takahashi et al. ............... 204/603

FOREIGN PATENT DOCUMENTS 9604547  2/1996  WIPO .

OTHER PUBLICATIONS

D. Jed Harrison et al, "Micromachining a Miniaturized Capillary Electrophoresis–Based Chemical Analysis System on a Chip" Science, vol. 261 (13 Aug. 1993) 895–897.

Primary Examiner—William H. Beisner
Assistant Examiner—John S. Stavsiak, Jr.
Attorney, Agent, or Firm—Dann Dorfman Herrell and Skillman; Morgan & Finnegan

[57] ABSTRACT

A microchip device includes a focusing channel, in which an electric field strength established in the focusing channel is controlled relative to an electric field strength established in a material transport channel segment to spatially focus the material traversing the material transport channel segment.

21 Claims, 11 Drawing Sheets

APPARATUS AND METHOD FOR PERFORMING ELECTRODYNAMIC FOCUSING ON A MICROCHIP

This invention was made with Government support under contract DE-AC05-84OR21400 awarded by the U.S. Department of Energy to Lockheed Marietta Energy Systems, Inc. and the Government has certain rights in this invention.

FIELD OF THE INVENTION

The present invention relates generally to miniature instrumentation for chemical analysis and chemical sensing and, more specifically, to electrically controlled spatial focusing of material manipulations in microchip or related structures. These manipulations can be used in a variety of applications, including the electrically controlled manipulation of fluid for capillary electrophoresis, liquid chromatography, and flow injection analysis.

BACKGROUND OF THE INVENTION

It is known to form micron-sized channels in substrates, such as microscope slides, for the purpose of performing a variety of chemical measurements. These substrates, with patterned channels, have come to be known as "microchips."

To date, micromachined fluid pumps have had limited performance and are not appropriate for many microchip applications. Other mechanisms of material transport, such as electrokinetic phenomena, i.e., electroosmosis and electrophoretic transport, are of interest due to the ease with which they can be incorporated into microfabricated devices.

With microchip devices, several applications require the ability to precisely spatially confine a sample with consistent reproducibility. To this end, related co-pending application Ser. No. 08/283,769 filed Aug. 1, 1994 provides a structure for electrically providing material transport through microchip structures with very good spatial confinement.

Examples of microchip devices and methods can be found in the following: U.S. Pat. No. 5,296,114 to Manz; "Micromachining a Miniaturized Capillary Electrophoresis-Based Chemical Analysis System on a Chip," by D. J. Harrison et al., *Science*, Vol. 261 (Aug. 13, 1993); "Glass Chips for High-Speed Capillary Electrophoresis Separations with Submicrometer Plate Heights," by C. S. Effenhauser et al., *Anal. Chem.*, 65, 2637–2642 (1993); "Effects of Injection Schemes and Column Geometry on the Performance of Microchip Electrophoresis Devices," by S. C. Jacobson et al., *Anal. Chem.*, 66,1107–1113 (1994); and "Open Channel Electrochromatography on a Microchip," by S. C. Jacobson et al., *Anal. Chem.*, 66, 2369–2373 (1994).

While the foregoing publications describe general techniques and devices for performing fluidic manipulations, a continuing need exists for improvements in "electrodynamic focusing." Electrodynamic focusing refers to the use of electrokinetic transport to confine spatially the transport of both fluids and ions. Electrodynamic focusing differs from hydrodynamic focusing which uses pressure driven flow to confine the sample stream. Electrodynamic focusing includes the forces from electroosmotic fluid flow and electrophoretic forces due to electrostatic fields. In the context of this invention, sample stream implies the transport of a sample material either by electroosmotic flow, electrophoretic motion, or both.

SUMMARY OF THE INVENTION

An object of the present invention is to provide a miniaturized apparatus and method which uses electrostatic forces to spatially shape a sample stream, making it small in lateral spatial extent and stable with time.

These and other objects of the invention are met by providing a method of controlling material transport in an interconnected channel structure having at least three ports, which includes actively controlling the electric potential at the at least three ports to spatially control the lateral dimensions of a sample stream.

Other objects, advantages and salient features of the invention will become apparent from the following detailed description, which taken in conjunction with the annexed drawings, discloses preferred embodiments of the invention.

DETAILED DESCRIPTION OF THE INVENTION

The microchips described herein are fabricated using standard photolithographic, wet chemical etching, and bonding techniques that were described in related application Ser. No. 08/283,769 filed Aug. 1, 1994, which is hereby incorporated by reference.

Figure 1:
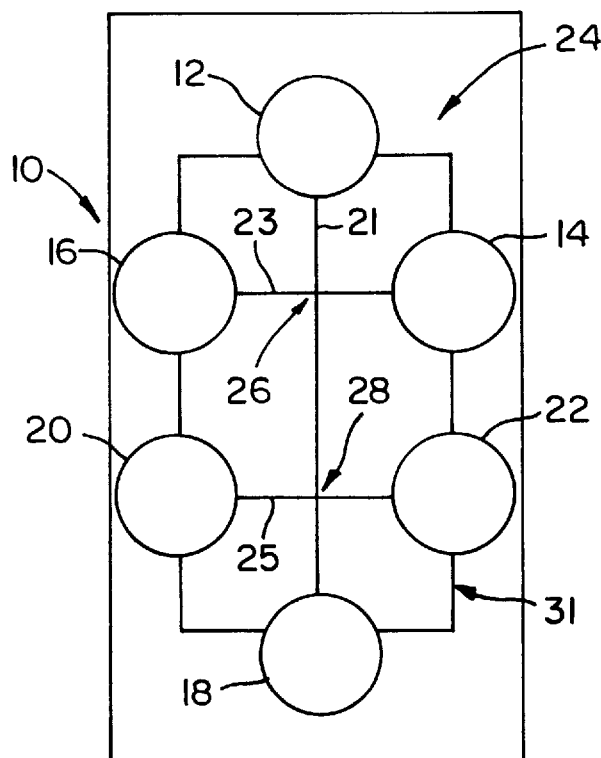
FIG. 1 is a schematic top view of a microchip according to a first preferred embodiment of a microchip according to the present invention.

Referring to FIG. 1, a microchip 10 includes a plurality of reservoirs including sample reservoir 12, a sample waste reservoir 14, a buffer reservoir 16, a waste reservoir 18, and focusing reservoirs 20, 22. A channel structure is generally referred to by the numeral 24 and includes channel segments 21, 23, and 25 that intersect at two significant locations which have been designated the "sample injection cross" 26 and the "focusing chamber" 28.

The channels are formed in a substrate 30, which may be a glass microscope slide, for example, and are covered with a cover plate 31, which is shown in this case as having a rectangular perimeter smaller than the rectangular perimeter of the substrate 30.

The column design is transferred onto the substrate 30 using a positive photoresist, photomask, and UV exposure. The channels are etched into the substrate in a dilute, stirred $HF/NH_4F$ bath. To form the closed network of channels, the cover plate is bonded to the substrate 30 over the etched channels by hydrolizing the surfaces, bringing them into contact with each other, and processing thermally to 500° C.

In experiments conducted with different microchips, designated "A, B, and C," different microchip dimensions were employed. The microchip channels had, in the case of microchip A, a width at half-depth of 18 $\mu$m and a depth of 6.4 $\mu$m, in the case of B 64 $\mu$m and 9 $\mu$m, and for C, 70 $\mu$m and 7.6 $\mu$m. These dimensions were measured using a stylus-based surface profiler.

The reservoirs are affixed with epoxy at the point where the channel extends beyond the cover plate. The electroosmotic mobility for microchips A and B are that of native glass, but electroosmotic mobility is minimized for microchip C by covalent immobilization of linear polyacrylamide using standard procedures.

Figure 3:
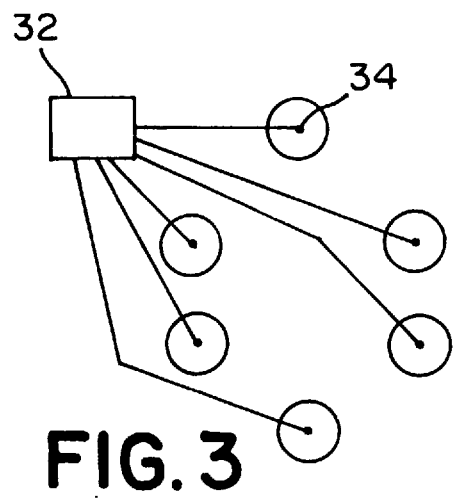
FIG. 3 is a schematic view showing electrical connections between the various reservoirs of the microchip and a voltage source.

As shown schematically in FIG. 3, each reservoir is coupled to a voltage source 32 through platinum wires 34 that extend into the reservoirs.

To monitor performance of the electrodynamic focusing on microchips, an experimental setup was established by using laser induced fluorescence (LIF) using a charge coupled device (CCD) for imaging. For CCD imaging, an argon ion laser beam (514.5 nm, 100 mW) was used and expanded to ≈5 mm diameter at the microchip surface using a lens. The fluorescence signal was collected using an optical microscope, filtered spectrally (550 nm cut-on), and measured by the CCD. A buffer used had 10 mM sodium tetraborate, and test samples used were rhodamine 6G (40 $\mu$M), rhodamine B (40 $\mu$M), and disodium fluorescein (50 $\mu$M) in 10 mM buffer.

The experiments were performed under continuous infusion of sample from reservoir 12 through the focusing chamber 28. The microchip 10 is capable of performing injections using injection cross 26, but only the spatial transport characteristics of the focusing chamber were studied.

The invention entails using the focusing reservoirs 20 and 22 to laterally focus the sample transported from sample reservoir 12 to waste reservoir 18. The electric potentials at the sample reservoir 12, and focusing reservoirs 20 and 22 are controlled independently with multiple voltage sources. An example of such sources would be multiple dc/dc converters, each capable of converting output voltages as appropriate. Alternatively, a single voltage source in conjunction with an appropriate voltage divider could provide the multiple outputs. For cathodic eletroosmotic flow, as with native glass surfaces, the waste reservoir 18 is in general at a lower potential than all other reservoirs, and in this case, grounded. No potential is applied to the buffer and sample waste reservoirs 16 and 14, i.e., the reservoirs are electrically floated.

Figure 2:
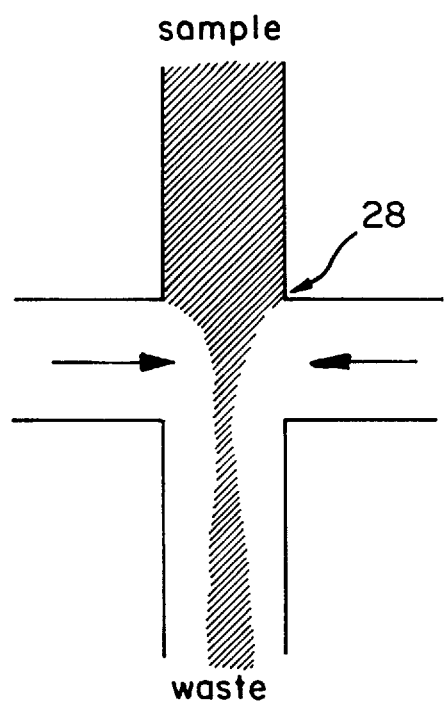
FIG. 2 is an enlarged view of the electrodynamic focusing area of the microchip of FIG. 1 with the shaded area indicating the general transport pattern of a sample fluid traversing from top to bottom in the vertical channel.

The relative potentials at the reservoirs are varied to enhance or diminish the degree of focusing. FIG. 2 shows schematically the focusing effect on the stream of sample material (which is shown as cross-hatched) at the focusing chamber 28. The sample is introduced through the channel on top in a continuous fashion. Either hydrodynamic and/or electrostatic forces from the two side channels, from focusing reservoirs 20 and 22, laterally confine the sample stream. The sample stream reaches a minimum transverse dimension and then broadens due to diffusion after leaving the focusing chamber.

Differences in channel lengths and widths require different voltages to be applied to the focusing reservoirs 20 and 22 to balance the field strengths and to obtain a symmetric fluid flow in the focusing chamber. The sample field strength is defined as the electric field strength in the sample channel 23, and correspondingly, the focusing field strength is the electric field strength in the focusing channels 25. All sample stream profiles are measured at full width half maximum ("fwhm").

Figures 4A, 4B, 4C, 4D:
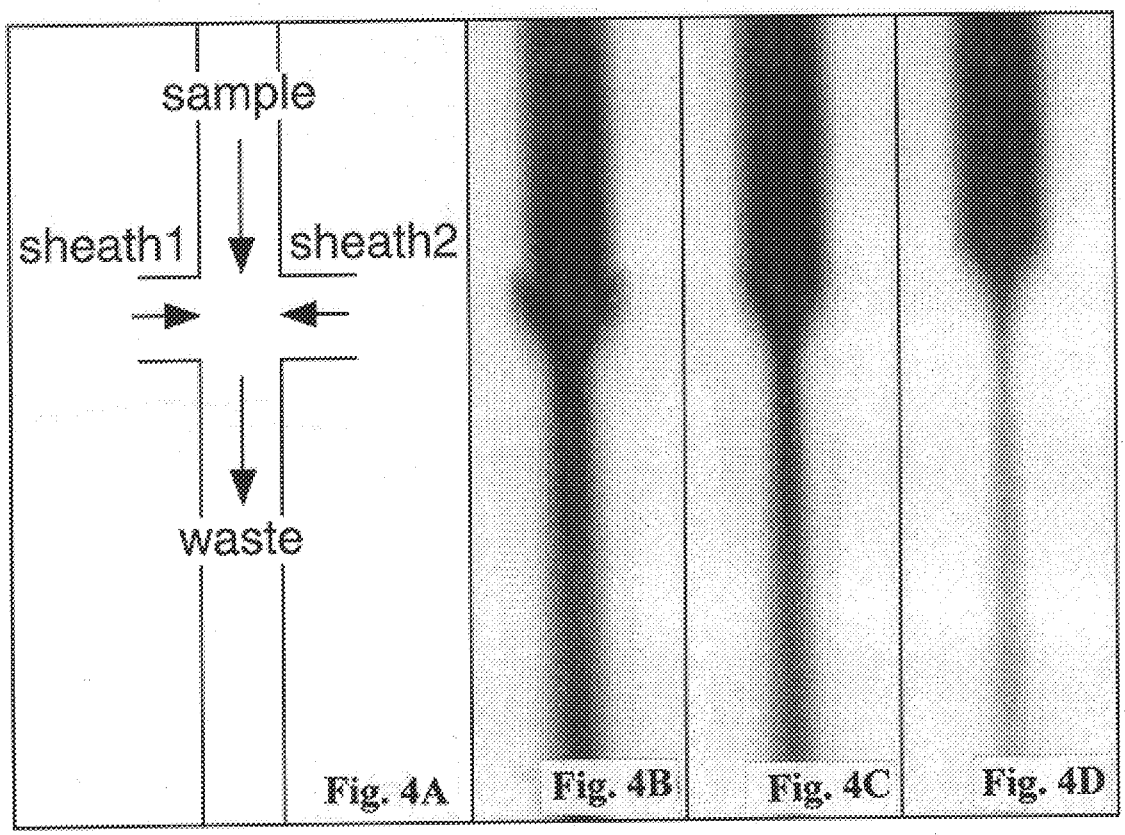
FIG. 4($a$–$d$) show CCD images of electrodynamic focusing for rhodamine 6G using the method and apparatus of the present invention, with the arrows showing force direction when the applied potentials to the focusing reservoirs 20 and 22 and waste reservoir 18 are at 2.4, 2.6, and 0 kV, respectively, and with the sample reservoir 12 potential varied from 3.9 to 1.9 kV.

To demonstrate visually the two-dimensional spatial focusing, CCD images show the sample focused to widths of 9.2 $\mu$m, 5.6 $\mu$m, and 3.3 $\mu$m in FIGS. 4(b), 4(c) and 4(d), respectively, using microchip A. The focusing chamber is defined as the region where the two channels intersect, and for microchip A the chamber is 18 $\mu$m long by 18 $\mu$m wide. The shaded regions in the images are the sample, rhodamine 6G. For these profiles, the potential at the focusing reservoirs 20 and 22 are held constant with the voltage at the sample reservoir 12 varied, decreasing from image 4(b) to 4(d).

Figure 5:
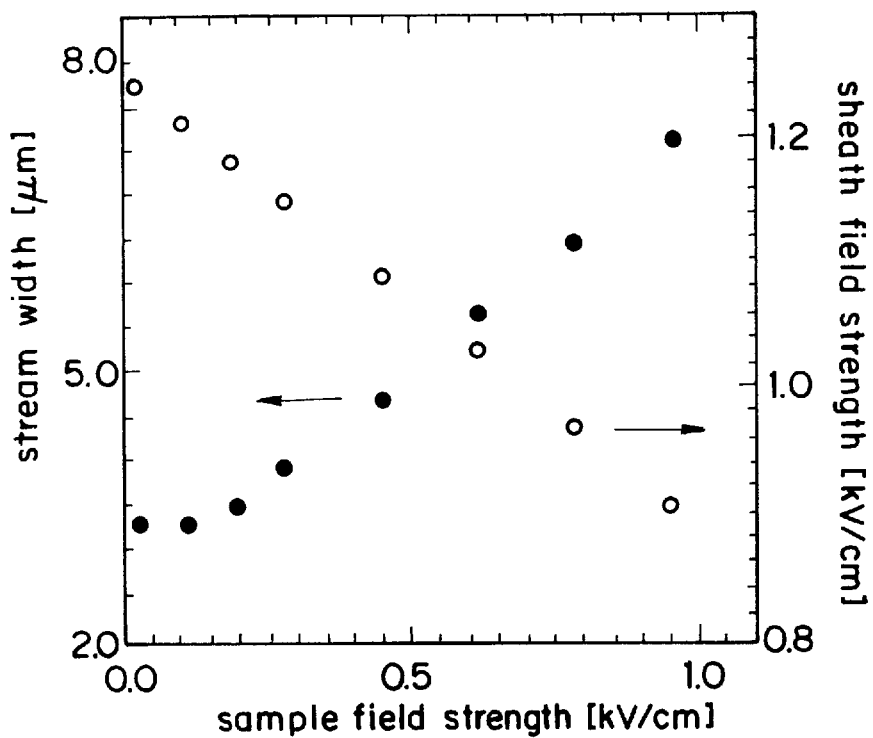
FIG. 5 is a graph showing variation of sample stream width (rhodamine 6G), as the solid circle, and focusing field strength, as the hollow circle, versus sample field strength in microchip A with 2.4 and 2.6 kV applied to focusing reservoirs 20 and 22, respectively.

As the potential at the sample reservoir is decreased, the sample field strength decreases, and the focusing field strength increases resulting in a tighter focus of the sample stream as shown in FIG. 5.

In FIGS. 4(b), (c), and (d), the sample field strengths are 1.12, 0.61, and 0.11 kV/cm, respectively, and the focusing field strengths are 0.85, 1.01, and 1.16 kV/cm, respectively. Sample transport through the focusing chamber 28 stops when the potential at the intersection exceeds the potential applied to the sample reservoir, i.e., the direction of transport in the sample channel reverses.

Figure 6:
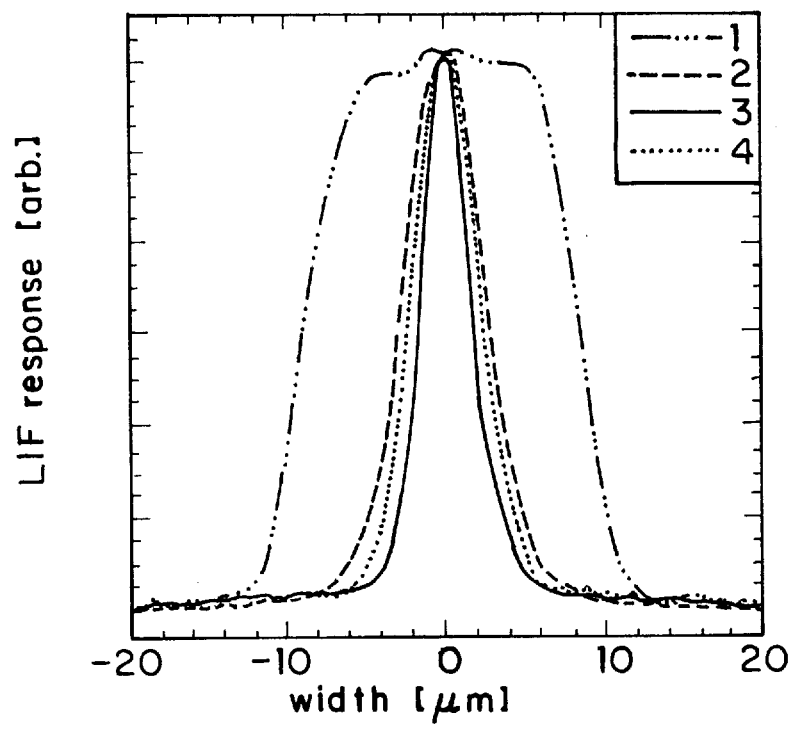
FIG. 6 is a graph showing sample stream profiles taken at 3 $\mu$m upstream from the focusing chamber (profile 1), 9 $\mu$m into the chamber (profile 2), 18 $\mu$m into the chamber (the point of tightest focus) (profile 3), and 60 $\mu$m downstream of the chamber (profile 4)(these profiles are extracted from the image of FIG. 4($d$) with the amplitudes normalized to compare sample stream widths—the focusing chamber begins at the top of the intersecting channels and concludes at the bottom)

In FIG. 6, the intensity profiles are extracted from the image in FIG. 4(d). The profiles are normalized in order to compare peak widths for the sample before the focusing chamber, in the chamber, and below the chamber. Profile 1 is taken before the sample enters the focusing region and is 3 μm above the intersection. This profile is similar for any cross-section taken along the sample channel. Profile 2 is 9 μm into the chamber, i.e., in the center of the focusing chamber, and shows substantial focusing.

Profile 3 is 3.3 μm wide (fwhm) and is 18 μm into the focusing cell, i.e., at the exit of the chamber. Profile 4 is 60 μm below the focusing chamber and is broadened slightly relative to profile 3 due to diffusion.

Figure 7:
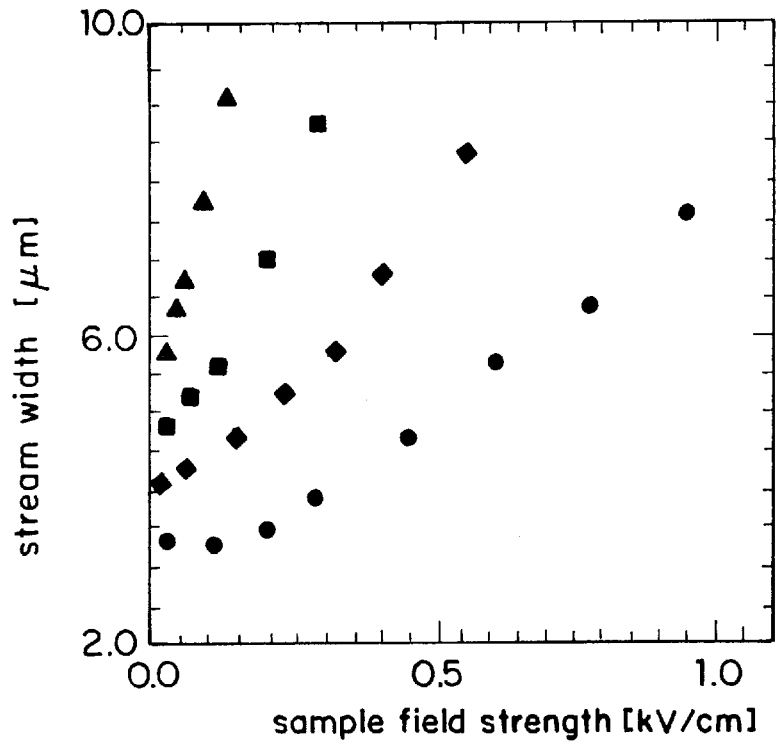
FIG. 7 shows a variation of sample stream width versus sample field strength for rhodamine 6G with 0.31 and 0.33 kV (▲), 0.61 and 0.65 (■), 1.2 and 1.3 kV (♦), and 2.4 and 2.6 kV (●) applied to the focusing reservoirs 20 and 22, respectively, of microchip A.

In FIG. 7, the variation of the sample stream width is plotted with increasing sample field strength for four different sets of potentials applied to the focusing reservoirs 20 and 22. Essentially, as the field strength in the focusing channels increases, the degree of focusing increases. For example, with 0.31 and 0.33 kV applied to the focusing reservoirs 20 and 22, respectively, the sample width is 3.3 μm, and the focusing field strength is 1.20 kV/cm. A 1.8-fold decrease in the sample stream width is observed for an 8-fold increase in the focusing field strength. In addition, only for the highest focusing potential (2.4 and 2.6 kV, respectively) does the stream width appear to be asymptotically approaching a minimum in FIG. 7. The sample width is also dependent upon the width of the sample channel.

Figure 8:
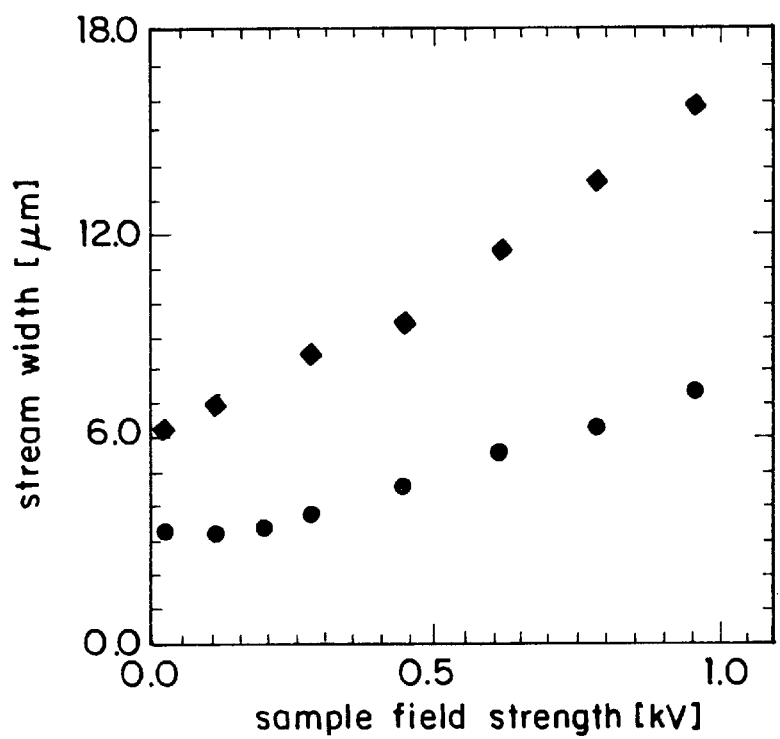
FIG. 8 is a graph illustrating a variation of sample stream width versus sample field strength for rhodamine 6G (●) and rhodamine B (♦) using microchip A.

In FIG. 8, the sample widths are compared for two microchips with sample channel widths of 18 μm for microchip A and 64 μm for microchip B. The minimum sample stream widths are 3.3 μm for microchip A and 6.3 μm for microchip B. For a 3.6 fold decrease in channel width, the sample stream width for microchip A is only 1.9 times narrower than for microchip B. Comparable focusing field strengths of 1.2 and 1.25 kV/cm are used for microchip A and B, respectively.

This quadratic dependence between sample width and channel width can be qualitatively understood if the transverse focusing force is assumed to be constant over the width of the channel and that force is opposed by diffusion. The sample and focusing channels are assumed to be of equal width, and the electric field strengths are equivalent, as in the experiments. The focusing force is applied for a proportionally longer time with wider channels and likewise diffusion has a longer period over which to spread the sample stream with the diffusion distance depending on the square root of time. The focusing for the wider channel of microchip B does not appear to reach a minimum stream width as it does with microchip A.

Figure 9:
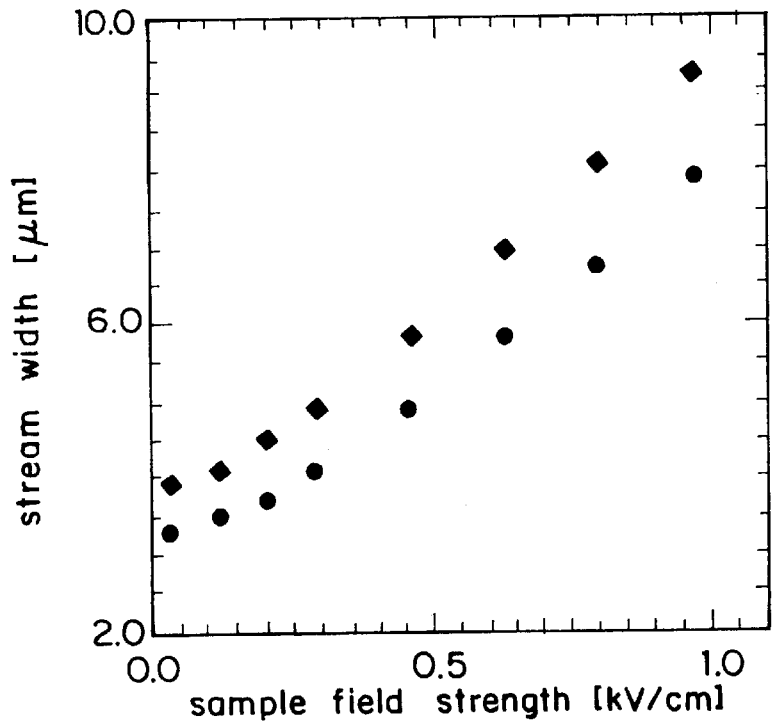
FIG. 9 is a graph illustrating a variation of sample stream width versus sample field strength for microchip A with a channel width of 18 $\mu$m (●) and for microchip B with a channel width of 64 $\mu$m (♦), where rhodamine 6G was the sample.

In FIG. 9, the focusing of a cationic dye, rhodamine 6G, and a neutral dye, rhodamine B, are compared. An anionic dye, fluorescein, could not be focused to the same degree as the cationic dye. These samples are used to compare focusing by hydrodynamic and electrophoretic forces. Using a focusing field strength of 1.20 kV/cm and a sample channel field strength of 37 V/cm, the sample widths are 3.3 μm for rhodamine 6G and 3.9 μm for rhodamine B. The 0.6 μm difference is presumably due to the additional electrophoretic contribution to focusing in the case of the cationic dye.

Figure 14:
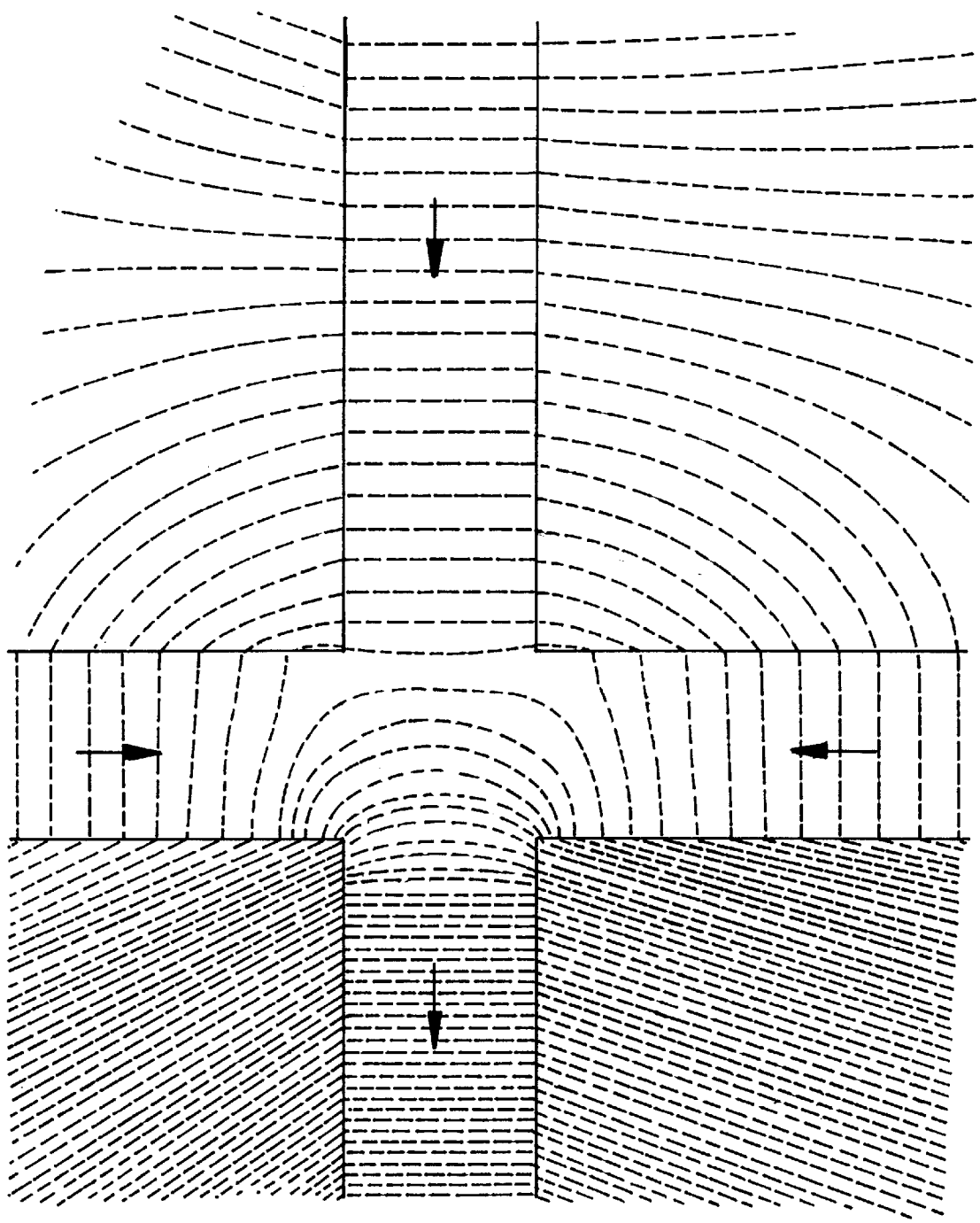
FIG. 14 shows the equipotential lines for the sample and focusing channels, and the focusing chamber, with the directional arrows depicting the direction of the potential gradients.

It can be shown theoretically that one would expect spatial focusing of ions by purely electrophoretic forces using the focusing chamber arrangement described in FIG. 2. FIG. 14 shows the equipotential lines for the sample and focusing channels, and the focusing chamber. The sample channel is vertical with sample transport from top to bottom as indicated by the arrows. The arrows also indicate the desired gradient of the electrical potential, or the electric field strength, in the channels. The horizontal channels are the focusing channels providing the focusing force upon the sample traversing the focusing chamber. The broken lines in this figure are the equipotential lines as determined by solving Laplace's equation for a potential distribution as typically used in an electrodynamic focusing experiment. A step from one line to the next indicates a fixed change in electric potential. Therefore the closer the line spacing, the greater the electric field strength.

Figure 15:
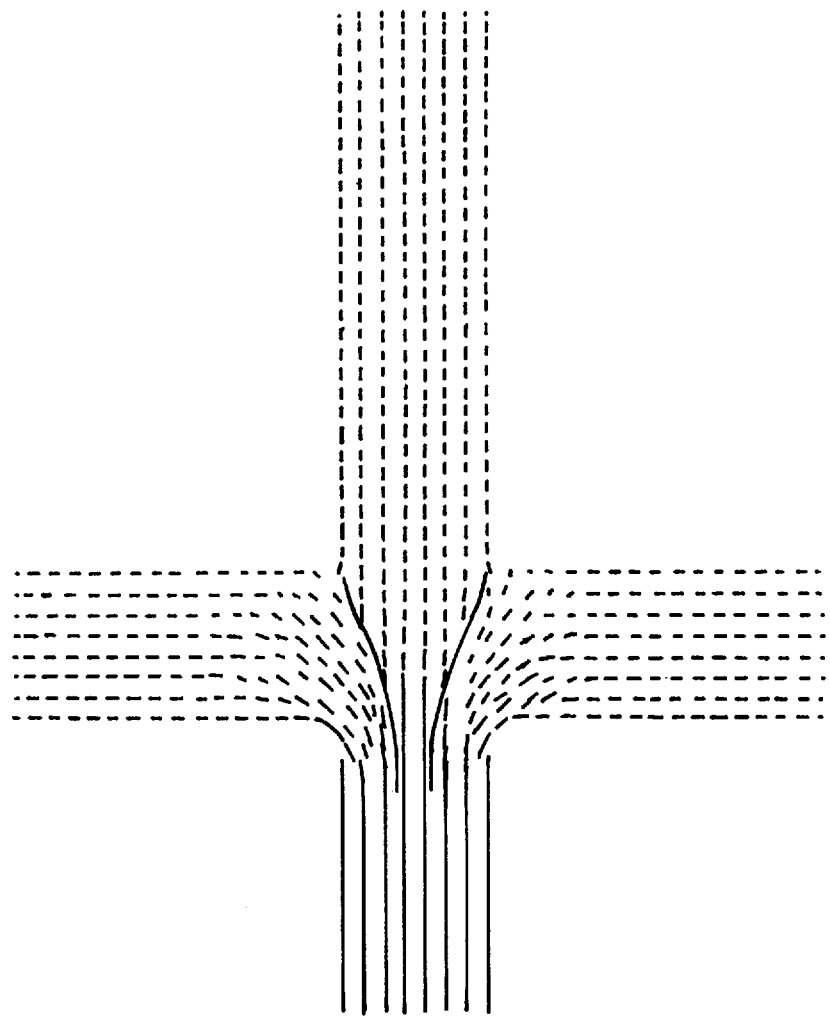
FIG. 15 is the result of a calculation where the direction and length of the line segments show the electric field vector direction and magnitude, respectively.

The electric field can be calculated from FIG. 14 by finding the gradient of this electric potential surface. FIG. 15 is the result of such a calculation where the direction and length of the line segments show the electric field vector direction and magnitude, respectively. The lines run together below the focusing cell due to the increase in electric field strength. The trajectories of ions that enter the focusing cell from the extreme edges of the sample channel are sketched in FIG. 15 as solid curves. The trajectory lines are drawn by iteratively using the previous electric field vector line segment to show the trajectory for arriving at the next electric field vector line segment. Clearly, the electric field in the focusing chamber will force ions to be transversely confined even though there is no bulk fluid flow.

Figure 10:
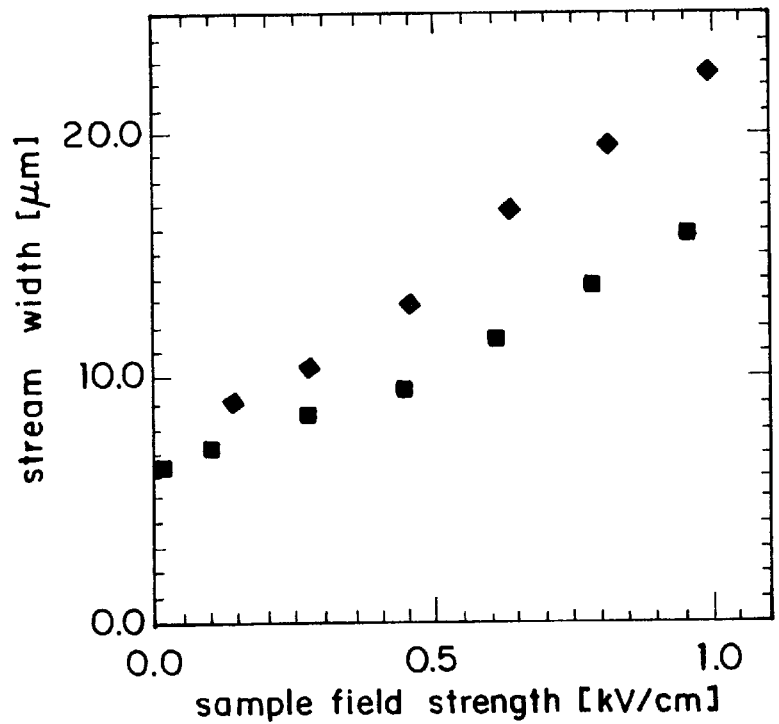
FIG. 10 illustrates a variation of sample stream width versus sample field strength for microchip B with electroosmotic flow (■) and microchip C without electroosmotic flow (♦), where rhodamine 6G was the sample.

In FIG. 10, sample focusing is performed with and without electroosmotic flow. In the case where electroosmotic flow is minimized by the presence of covalently immobilized linear polyacrylamide on the channel walls, electrophoretic forces are predominantly responsible for focusing the sample.

For demonstration of electrophoretically driven electrodynamic focusing, microchip B with native glass channels was compared to microchip C with channels of similar cross section but with the channel walls modified with linear polyacrylamide to diminish the electroosmotic flow. For microchip B, with a sample channel width of 64 μm, the focusing field strength is 1.25 kV/cm and the sample channel field strength is 17 V/cm which results in a sample stream width of 6.3 μm. For microchip C, with a sample channel width is 70 μm, the focusing field strength is 1.3 kV/cm and the sample channel field strength is 150 V/cm which gives a sample width of 9.1 μm. The addition of electroosmotic flow narrows the sample a factor of ≧1.4 times narrower than without electroosmotic flow using comparable microchips.

A perpendicular channel arrangement may not be the optimum focusing chamber geometry, and focusing forces introduced at acute angles relative to the sample channel may lead to tighter focusing. Focusing may also be improved by increasing the width of the focusing channels relative to the sample channel.

Devices which incorporate three dimensional electrodynamic focusing should further reduce both the probe volume and the signal background from the substrate material for fluorescence measurements.

Electrodynamic focusing can also be performed with sample and focusing buffers having different conductivities. By having a sample in a buffer with a lower conductivity than the focusing buffer, stacking of the sample at the boundary between the two buffers occurs. Consequently, a concentration enhancement can be observed in addition to confinement of the sample by the focusing buffers.

Figure 12:
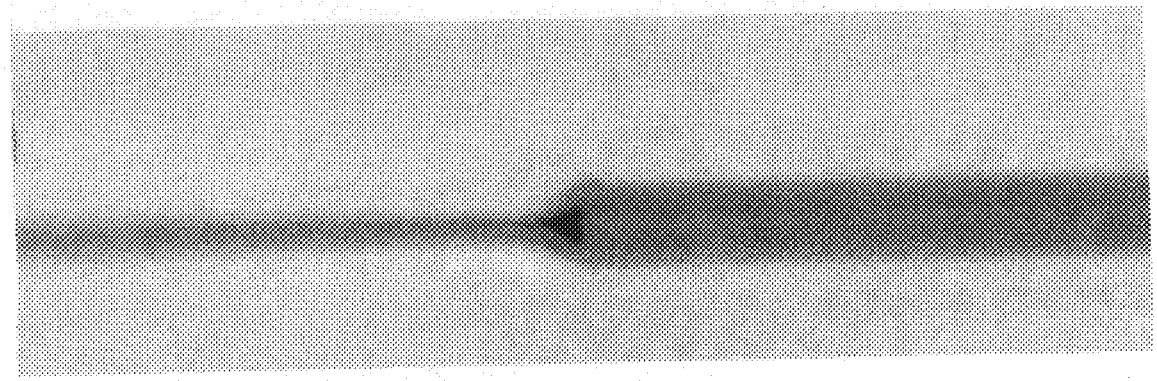
FIG. 12 shows an image of an electrodynamic focusing experiment with a "stacking" feature.

FIG. 12 shows an image of an electrodynamic focusing experiment with a "stacking" feature. In this figure, the sample channel is horizontal with material transport from right to left, i.e., the sample reservoir is connected to the channel leading to the right and a waste reservoir to the channel leading to the left.

The focusing channels are obviously positioned vertically at the center of the image where the fluorescent (gray) material is spatially confined to a more narrow transverse dimension. In this experiment the sample solution is 45 $\mu$M R6G in 50 $\mu$M borate and the focusing buffer is 10 mM borate. Microchip A is used with the 3.0 kV applied to the sample reservoir and approximately 2.5 kV to the focusing reservoirs. It is obvious in the image of FIG. 12, where a darker shade of gray indicates a more intense fluorescence image, that the sample is not only focused but concentrated within the focusing cell.

Figure 13:
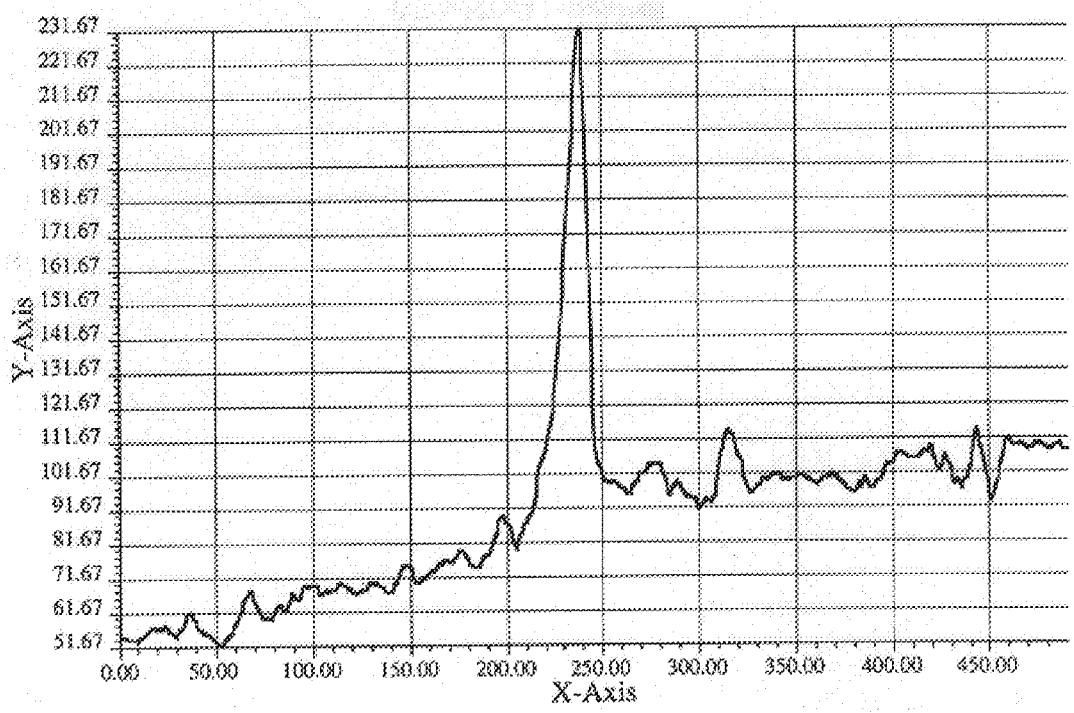
FIG. 13 is a plot of the signal intensity at the CCD pixels for a line going through the center of the sample channel in FIG. 12.

FIG. 13 is a plot of the signal intensity at the CCD pixels along a line going through the center of the sample channel in FIG. 12. The fluorescence signal increases a factor of 2–5 as the sample traverses the focusing cell. It may also be possible to use buffers differing in ionic strength to achieve greater focusing than with homogeneous buffer systems.

Figure 16:
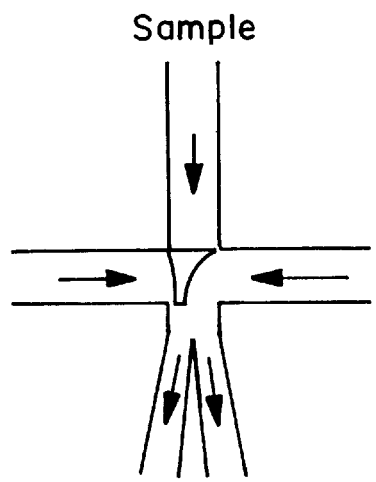
FIGS. 16 and 17 are schematic views showing application of a sample or cell sorting technique according to the present invention.
Figure 17:
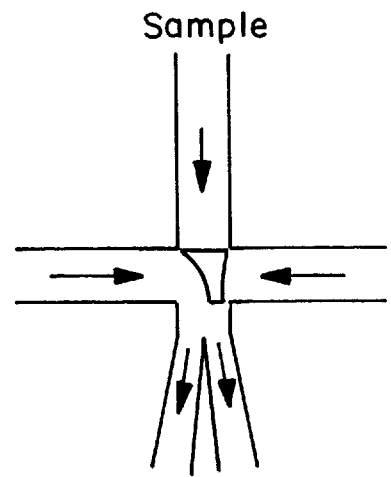

The sample stream could be further manipulated by controlling the relative strengths of the electric fields in the two focusing channels. An application of such a manipulation procedure is shown in FIGS. 16 and 17. The basic four way intersection is again used as a focusing chamber but the lower sample channel is bifurcated into two channels, slightly below the intersection, with either common or separate reservoirs depending on the application.

Electric potentials are applied to achieve sample transport in the direction of the arrows. Two different cases are shown in FIGS. 16 and 17, where the spatial extent of the sample in the focusing chamber is shown by the shading. In FIG. 16, the focusing field strength on the right is larger than on the left as indicated by the relative size of the arrows. The sample profile is pushed to the left and into the left-hand lower channel. Alternatively, the relative magnitude of the focusing field strengths can be reversed to push the sample into the right lower channel. Such manipulations would be useful in cell or molecular sorting experiments. The sample would be interrogated in the focusing chamber or before and depending on the result of that interrogation, the sample would be sent to the right or left lower collection channels. The same result might also be achievable by using separate reservoirs on the lower collection channels and grounding the reservoir in which the sample is to be collected. Using this method of sorting one could either leave the focusing fields fixed or alternate them as described above.

The devices and methods described herein have many varied uses, such as flow cytometry as a stand alone miniaturized device, or incorporated into miniaturized systems. Flow cytometry is widely used in research and clinical diagnostic settings. In general, the microchannel structure described above is preferably made of optically transparent material, so that once a sample of material has been spatially focused, an optical measuring system can be employed to quantify or qualify the sample.

Figure 11:
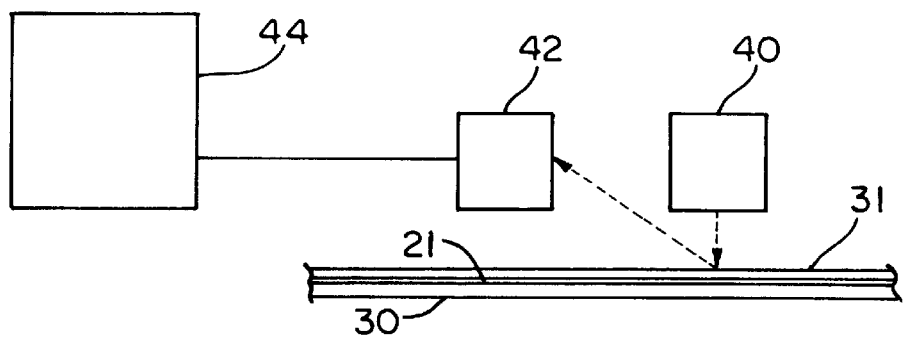
FIG. 11 is a schematic view of a diagnostic or testing apparatus employing the microchip apparatus of FIG. 1.

Referring to FIG. 11, which is a schematic view of a testing apparatus, the substrate 30 and cover plate 31 are made of transparent material. Thus, the sample (such as biological cells) in channel 21 can be irradiated with light from a light source 40. For many analyses, a laser is the preferred light source. The laser beam is focused at the point of tightest lateral spatial focusing, which is the narrowest width of material shown in FIG. 2 at the intersection. Once irradiated with light, a light detector 42 can be used to detect elastically or inelastically scattered light or fluorescence. This detected light can be analyzed with any suitable instrument 44, such as a computer programmed to perform various data analyses. The nature of the detected light can be correlated to a condition or property of the sample. Methods of detection other than electromagnetic energy may be possible, such as electrochemical detection.

The electric fields established to impart fluid transport are dependent on the electrical characteristics of the materials being transported, the buffers employed, and the chip itself. For example, native glass is normally negatively charged, but it can be chemically treated so that the channels are positively charged. Thus, depending on these parameters, the polarity of the voltages can be either positive or negative.

The electrodynamic focusing effects described herein have been described with reference to micromachined channel structures formed in a substrate. It is within the scope of the present invention to realized electrodynamic focusing effects in conventionally formed capillaries and channels and other forms of material or fluid conduits. In the above description the use of the word channel refers to conduits of all types that are of a cross sectional dimension of several millimeters or less. It is also clear that a hybrid approach to electrodynamic focusing could be implemented that uses hydraulic flow to either provide the material transport or the focusing force with the other (material transport or focusing) provided by electrokinetic forces.

Figure 18:
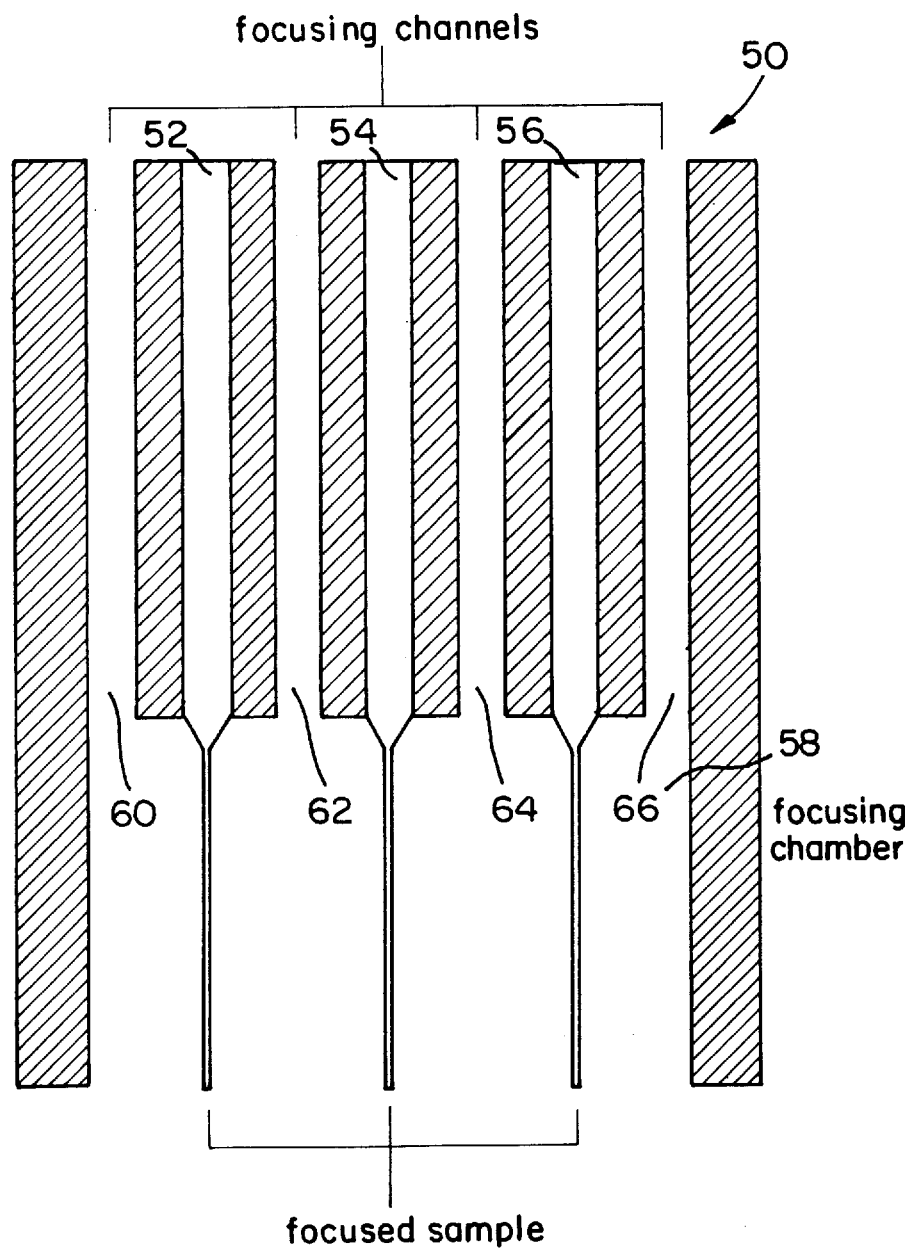
FIG. 18 is a sectional view of a multiplex microchip according to another embodiment of the present invention.

The focusing chamber can also be multiplexed on a planar surface to achieve lateral spatial confinement of more than one sample stream. Referring to FIG. 18, which is an enlarged sectional view of a multiplex microchip 50, three sample channels 52, 54, 56 contain a material to be analyzed and terminate in a focusing chamber 58. Focusing channels 60, 62, 64 and 66 are disposed on opposite sides of the respective sample channels.

As shown in FIG. 18, the sample becomes focused where the sample exits the sample channels due to electrokinetic forces. The three sample streams are axially transported down the sample channels and are laterally confined by the buffer in the adjacent focusing channels. Lateral confinement occurs when the flow of buffer in the focusing channels is greater than the flow of sample in the sample channels. The two focusing channels in the middle of the microchip serve to confine the sample streams in the two adjacent sample channels conserving the total number of focusing channels needed.

As in the other embodiments, the channels are connected to voltage sources to supply the necessary potentials to the buffer in the focusing channels and the samples in the sample channels. For example, upper ends of the sample channels may be in fluid communication with either distinct sample reservoir or a common sample reservoir. An electrode(s) could be inserted into the reservoirs to supply the electrical contact. Similarly, the upper ends of the focusing channels could be connected to a buffer reservoir or reservoirs, which could be coupled to a voltage source by an electrode inserted into the reservoir(s). Analysis of the samples can be performed in the region of the focusing chamber 58 by any known means.

This multiplexed electrodynamic focusing arrangement has applications to various analytical procedures, including high throughput DNA sequencing measurements. The spatial confinement allows high sensitivity fluorescence detection in a small probe volume and the parallel arrangement allows high sample throughput for electrophoretic sizing of sequencing products.

This design is not limited to three sample streams and four focusing streams but can be extended to handle as many sample streams as necessary. As many as 100 to 1,000 parallel channels may be desired for DNA sequencing applications.

Figure 19:
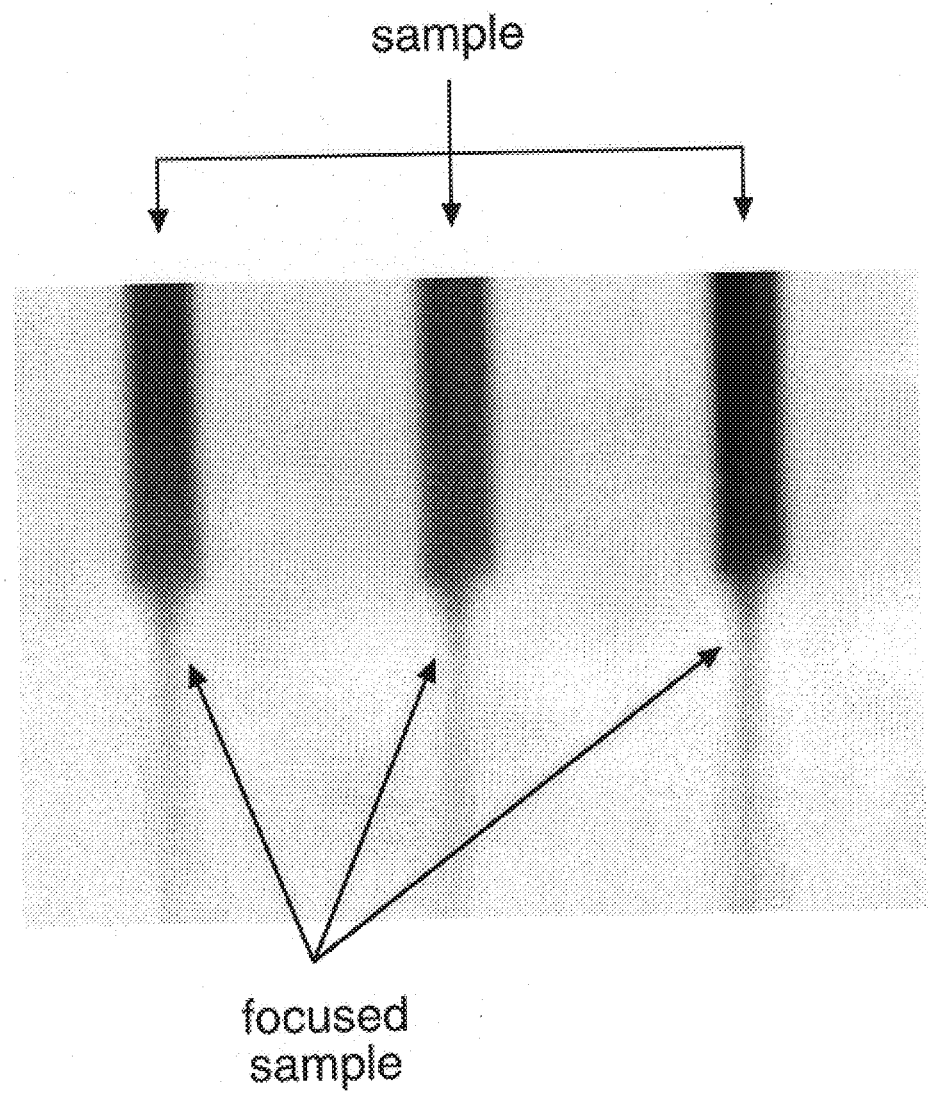
FIG. 19 illustrates experimental results using the microchip of FIG. 18.

Experimental results in the form of a CCD captured photomicrograph are shown for a multiplex electrodynamic focusing microchip in FIG. 19. The magnification is approximately 125× in this image. Three sample streams were focused simultaneously to an average width of 19 $\mu$m using a multiplexed focusing microchip schematically depicted in FIG. 18. The sample and focusing buffer channels had widths of 62 $\mu$m each and the focusing chamber had a width of 990 $\mu$m. The sample channels have a center-to-center spacing of 300 $\mu$m for the microchip imaged in FIG. 19. The sample is a 10 $\mu$m solution of rhodamine 6G in 10 $\mu$M borate buffer, and the focusing buffer is 10 $\mu$M borate buffer. The average focusing field strength in the four focusing channels is 880 V/cm, and the average sample field strength in the three sample channels is 130 V/cm. On this microchip the potential in each of the channels can be controlled individually, but a common reservoir could be employed for the sample and/or focusing buffer respectively.

While advantageous embodiments have been chosen to illustrate the invention, it will be understood by those skilled in the art that various changes and modifications can be made therein without departing from the scope of the invention as defined in the appended claims.

What is claimed is:

1. A method of spatially altering material for determining a property or condition of said material, comprising the steps of:
   applying a first electric potential to a material transport conduit, said applied first electrical potential inducing axially directed material transport;
   applying a second electric potential to a focusing conduit which forms a confluence with the transport conduit, said applied second electrical potential inducing lateral spatial confinement of the transported material at the confluence; and
   detecting a property or condition of the laterally spatially confined material.

2. A method according to claim 1, wherein the focusing conduit and the transport conduit are channels formed in a microchip, the focusing channel has first and second legs disposed on opposite sides of the transport channel and in opposing relation to each other, forming an intersection with said transport conduit, the second electric potential is applied to the first leg, and the method further includes applying a third electric potential to the second leg, the second and third electric potentials forming electric field vectors in general opposition to each other.

3. A method according to claim 1, wherein the focusing conduit and the transport conduit are channels which form an interconnected channel structure which includes a first reservoir, and a second reservoir, wherein the transport conduit is a first channel segment interconnecting the first and second reservoirs, a third reservoir, and a fourth reservoir, wherein the focusing conduit is a second channel segment interconnecting the third and fourth reservoirs and intersecting the first channel segment at an intersection, and the method further comprises the steps of applying electric potentials to the reservoirs to achieve lateral confinement, within the vicinity of the intersection, of the material transported through the first channel from the first reservoir.

4. A method according to claim 3, further comprising maintaining the electric potential at the intersection at a level lower than the potential at the first, third and fourth reservoirs and the second reservoir at a level lower than the potential at the intersection, said electrical potential levels effecting material transport in one direction from the first reservoir towards the second reservoir.

5. A method according to claim 1, wherein the transport conduit and the focusing conduit cross to form an intersection, and the method further comprises connecting a first reservoir to one end of the transport conduit, connecting a second reservoir to the opposite end of the transport conduit, connecting a third reservoir to one end of the focusing conduit, connecting a fourth reservoir to the opposite end of the focusing conduit, and applying electric potentials between at least two of the reservoirs to achieve lateral confinement, within the vicinity of the intersection, of the material transported through the transport conduit from the first reservoir.

6. A method according to claim 1, further comprising increasing the magnitude of the second electric potential relative to that of the first, said increased magnitude of the second electrical potential relative to the first electrical potential causing an increase in the degree of lateral confinement.

7. A method according to claim 1, wherein the first and second electric potentials impart at least one of electroosmotic flow and electrophoretic transport.

8. An apparatus for testing a sample of material comprising:
   at least one transport conduit and at least one focusing conduit, said at least one focusing conduit forming a confluence with said at least one transport conduit; and
   a voltage source for applying a first electric potential across said transport conduit and a second electric potential to said focusing conduit, said first electrical potential imparting axially directed material transport along said transport conduit and said second electrical potential imparting a lateral spatial confinement of the transported material at the confluence; and
   a detector for detecting a property or condition of said laterally spatially confined material.

9. An apparatus according to claim 8, wherein said voltage source is operable to increase the magnitude of the second electric potential relative to that of the first electrical potential, said increased magnitude of the second electrical potential relative to the first electrical potential causing an increase in the degree of lateral spatial confinement.

10. An apparatus according to claim 8, wherein the transport conduit and the focusing conduit are part of an interconnected channel structure which includes a first reservoir, a second reservoir, a first channel segment interconnecting the first and second reservoirs, a third reservoir, a fourth reservoir, and a second channel segment interconnecting the third and fourth reservoirs and intersecting the first channel segment.

11. An apparatus according to claim 10, wherein said voltage source is operable to electrically ground the second reservoir.

12. An apparatus according to claim 10, wherein said voltage source is operable to maintain the potential at the intersection at a level lower than the potential at the first, third and fourth reservoirs and the second reservoir at a level lower than the potential at the intersection, said potential maintaining means effecting material transport in one direction from the first reservoir towards the second reservoir.

13. An apparatus according to claim 8, wherein the focusing conduit forms a T-intersection with the transport conduit.

14. An apparatus for testing a sample of material which comprises a microchip device comprising:
   (i) a substrate having an interconnected channel structure formed thereon, the channel structure including a first reservoir, a second reservoir, a first channel segment interconnecting the first and second reservoirs, a third reservoir, a fourth reservoir, and a second channel segment interconnecting the third and fourth reservoirs and intersecting the first channel segment at a first intersection;
   (ii) a cover plate bonded to the substrate over the interconnected channel structure;
   (iii) means for applying voltages to the first, second, third and fourth reservoirs in relative magnitudes selected to laterally spatially confine material in one of the channel segments; and
   a detector for detecting a property or condition of said laterally spatially confined material.

15. A microchip device according to claim 14, further comprising a fifth reservoir, a sixth reservoir, a third channel segment interconnecting the fifth and sixth reservoirs and intersecting the first channel segment between the first reservoir and the first intersection.

16. A method of testing a sample of material comprising the steps of:
   placing the sample in a first reservoir which is connected to a second reservoir through a first channel;
   placing a buffer material in a third reservoir which is connected to the first channel through a second channel;
   placing a buffer material in a fourth reservoir which is connected to the first channel through a third channel disposed opposite the second channel, said first, second and third channels forming a four-way intersection;
   applying voltages to the first, second, third, and fourth reservoirs to achieve lateral spatial confinement of the sample in the first channel;
   exposing the spatially confined sample to electromagnetic energy whose interaction characteristics vary in accordance with at least one property or condition of the sample.

17. A method according to claim 16, wherein the exposing step comprises focusing a laser beam at a spot centered on the lateral spatial confinement of the sample, measuring at least one of the elastic or inelastic scattering, fluorescence, or absorbance attributable to interaction between the sample and the laser beam, and correlating characteristics of the light to at least one property or condition of the sample.

18. A method according to claim 17, wherein the sample material is a sample of biological cells.

19. An apparatus for sorting material comprising:
   a microchannel structure having a material transport segment with a distal end in communication with a material reservoir, first and second focusing segments disposed on opposite sides of the transport segment, each having a distal end in communication with first and second focusing reservoirs, respectively, and a proximal end forming an intersection with a proximal end of the transport channel, and at least two sorting segments having proximal ends disposed in proximity to, and in fluid communication with, the intersection;
   a voltage source for establishing a first electric field vector to axially transport material in the transport channel, and second and third electric field vectors to laterally confine and manipulate the material into one of the two sorting segments.

20. An apparatus according to claim 19, wherein the voltage source is operable to effect grounding of the receiving reservoir and electrical floating of the reservoir connected to the other sorting segment, said grounding and electrical floating of said reservoirs causing the manipulation of material into one of the two sorting segments.

21. An apparatus for manipulating a sample, comprising:
   a plurality of spaced apart channels adapted to contain a fluid sample and having a common end terminating in a chamber;
   a plurality of focusing channels alternatingly disposed on opposite sides of the sample channels and being adapted to contain a fluid buffer and having a common end terminating in the chamber; and
   a voltage source for applying an electric potential to the focusing channels and the sample channels to impart axial motion of the sample towards the chamber and lateral spatial confinement of the sample in the chamber.

* * * * *